United States Patent
Seguine et al.

(10) Patent No.: US 6,185,450 B1
(45) Date of Patent: Feb. 6, 2001

(54) DIGITAL SLIDING POLE FAST-RESTORE FOR AN ELECTROCARDIOGRAPH DISPLAY

(75) Inventors: Dennis R. Seguine, Monroe; John R. Stice, Redmond; Stephen P. LaBrash, Seattle, all of WA (US)

(73) Assignee: Physio-Control Manufacturing Corporation, Redmond, WA (US)

( * ) Notice: Under 35 U.S.C. 154(b), the term of this patent shall be extended for 0 days.

(21) Appl. No.: 09/013,570

(22) Filed: Jan. 26, 1998

(51) Int. Cl.$^7$ ............................................. A61B 5/0428

(52) U.S. Cl. .......................................... 600/509; 128/901

(58) Field of Search .................................... 128/901, 902; 600/509, 510, 523; 607/4, 5, 9, 13

(56) References Cited

U.S. PATENT DOCUMENTS

| | | | |
|---|---|---|---|
| 4,467,813 | * | 8/1984 | Schomberg ........................... 128/902 |
| 4,811,738 | | 3/1989 | Economides et al. . |
| 4,903,700 | | 2/1990 | Whigham et al. . |
| 5,447,518 | | 9/1995 | Pless . |
| 5,470,342 | | 11/1995 | Mann et al. . |
| 5,531,769 | | 7/1996 | Fossan et al. . |
| 5,609,611 | | 3/1997 | Bolz et al. . |
| 5,620,466 | | 4/1997 | Haefner et al. . |

OTHER PUBLICATIONS

Linear Technology Brochure LTC 1479, "PowerPath Controller for Dual Battery Systems," 1996, pp. 1–24.

Description of an analog sliding pole from previous Physio–Control products, specifically the LIFEPAK 6, 9, 10, or 300, Jan. 15, 1997 or before.

* cited by examiner

Primary Examiner—George R. Evanisko
(74) Attorney, Agent, or Firm—Christensen O'Connor Johnson Kindness PLLC

(57) ABSTRACT

A method and apparatus for monitoring an electrocardiograph waveform, and for returning an electrocardiograph trace to the middle of a display, such as a chart recorder strip. The monitoring circuit includes an amplifier and a switch for switching the frequency response curve of the monitoring circuit. In a first position, the switch causes the monitoring circuit to have a slow frequency response curve, which allows for accurate monitoring of ECG waveforms. In a second position, the switch causes the monitoring circuit to have a fast frequency response curve, which allows the amplifier of the monitoring circuit to quickly be brought out of saturation. The amplifier of the monitoring circuit becomes saturated when a defibrillation or pace pulse has been applied to a patient who is being monitored. The switch is controlled by a pulse waveform control signal that is provided by a microprocessor. By varying the duty cycle of the control signal, the frequency response curve of the monitoring circuit can be shifted. By changing the duty cycle of the pulse waveform in incremental steps, certain problems can be avoided, such as erroneous QRS detect marks that are otherwise produced. The incremental steps in which the duty cycle of the pulse waveform is changed may be predetermined, or they may be adjusted according to feedback from the amplifier.

23 Claims, 9 Drawing Sheets

(NORMAL HEART BEAT)

(FIBRILLATING HEART)

(GENERAL METHOD)

(CALIBRATING METHOD)

DIGITAL SLIDING POLE FAST-RESTORE FOR AN ELECTROCARDIOGRAPH DISPLAY

FIELD OF THE INVENTION

This invention relates generally to a method and apparatus for monitoring an electrocardiograph waveform, and more particularly to a method and apparatus for returning an electrocardiograph trace to the middle of a display such as a chart recorder strip.

BACKGROUND OF THE INVENTION

One of the most common and life-threatening medical conditions is ventricular fibrillation, a condition where the human heart is unable to pump the volume of blood required by the human body. The generally accepted technique of restoring a normal rhythm to a heart experiencing ventricular fibrillation is to apply a strong electric pulse to the heart using a cardiac defibrillator.

To determine if defibrillation is required, defibrillators usually rely on an interpretation of an electrocardiograph (ECG) signal that is displayed on an ECG monitor or plotted on a strip of paper by a chart recorder. In such systems, the ECG signal is displayed as a waveform normally containing the P and T waves, as well as the QRS peaks associated with ventricular contraction. These waveforms are interpreted to determine the presence of ventricular fibrillation, ventricular tachycardia, asystole (the absence of contractions of the heart), or other abnormal heartbeat patterns.

One of the problems related to ECG monitoring is the typical situation where the ECG electrodes and certain tissues have become charged due to currents drawn through them during a pace pulse or defibrillation pulse. Once charged, the electrodes discharge over a time interval that may last up to several hundred milliseconds, depending upon the chemistry of the electrodes. As they discharge, the voltage across them is not DC, but rather an approximately exponentially decaying waveform, that is substantially larger than the normal range of ECG signals. Such voltages drive the amplifiers of the ECG monitoring circuit into saturation. Thus, a common problem is how to return as quickly as possible to normal ECG monitoring following the application of a defibrillation or pacing pulse which charges the electrodes and drives the amplifiers into saturation.

One prior art method for dealing with this problem is illustrated in U.S. Pat. No. 5,609,611 to Bolz et al., which discloses a pacemaker system with a porous electrode and residual charge or after-potential reduction. In addition, U.S. Pat. No. 4,811,738 to Economides et al. discloses a cardiac pacemaker with fast stored charge reduction. Both of these patents deal with the problem of trying to measure the electrical "response signal" of the heart (such as an ECG signal) during the period following a stimulation pulse. As stated in the patents, during each stimulation pulse, electrical charge is stored on the electrodes and in the polarization of the stimulated tissue that can interfere with normal heart measurements. Both disclosures describe techniques of providing short charges of opposite polarity following a stimulation pulse, so as to counteract the stored charge and quickly restore normal heart measurements. While these methods address the stored charge issue, they have disadvantages in that they require extra energy and time to implement the countercharges, and require additional countercharge circuitry.

Another prior art method is shown in U.S. Pat. No. 5,447,518 to Pless, which discloses a method and apparatus for phase-related cardiac defibrillation. As shown in FIG. 1 of Pless, the output from a first amplifier is coupled to a DC baseline restoring circuit including a resistor, a second amplifier, and a capacitor. The baseline restoring circuit has a variable time constant controlled by a microprocessor through a switch. When the switch is closed, current from the first amplifier is shunted through the resistor, thus providing a faster time constant. In addition, the second amplifier has a variable DC set point, which is also under the control of the microprocessor. In general, the sensing circuit generates a defibrillation output signal in response to an ECG signal of a certain level. After a defibrillation output signal is generated, the microprocessor sets the DC baseline restoring circuit to the rapid time constant by closing the switch. After a few milliseconds, the output of the amplifier is back to the same potential as it was just prior to the application of the defibrillation output signal. The microprocessor then opens the switch to return the baseline restoring circuit to the slower time constant. While this circuit addresses some of the problems raised regarding monitoring an ECG waveform following the application of a defibrillation pulse, it also has certain disadvantages. For example, in some systems, the method of instantly switching the baseline restoring circuit between rapid and slower time constants in the presence of decaying offsets tends to produce erroneous QRS detect marks (related to the QRS waveforms that indicate ventricular contraction) that could be interpreted as indicating a properly functioning heart, when in fact the heart is experiencing ventricular fibrillation. This could lead an operator to refrain from applying a defibrillation pulse when one is needed.

Accordingly, a method and apparatus are needed for returning to normal ECG monitoring as quickly and seamlessly as possible following delivery of defibrillation therapy. The method and apparatus should not require the output of additional energy or the presence of a significant amount of additional circuitry. In addition, the method and apparatus should return to normal monitoring without producing erroneous QRS detect marks. As explained in the following, the present invention provides a method and apparatus that meet these criteria and solve other problems in the prior art.

SUMMARY OF THE INVENTION

In accordance with the present invention, a digitally controlled circuit using a sliding pole is provided to restore an electrocardiograph (ECG) trace to the middle of a display. The ECG display includes a monitoring circuit with an amplifier and a switch that is controlled by a microprocessor. The switch is switchable between at least two states, the first state causing the monitoring circuit to have a first frequency response curve with a first pole, and the second state causing the monitoring circuit to have a second frequency response curve with a second pole. Thus, a selection of the frequency response of the monitoring circuit is controlled by the control signal for the switch, which is produced by the microprocessor.

In accordance with one aspect of the invention, the control signal for the switch is a pulse waveform with a variable duty cycle. By adjusting the duty cycle of the pulse waveform, the frequency response of the monitoring circuit can be adjusted. In one actual embodiment, the duty cycle of the pulse waveform is adjusted in incremental steps, so as to avoid the production of erroneous QRS detect marks that can otherwise occur. Also, the operating frequency of the pulse waveform is preferably above the upper frequency of the ECG bandwidth so that adjustments to the pulse waveform duty cycle do not produce erroneous QRS detect marks.

In accordance with another aspect of the invention, the amplifier of the monitoring circuit is brought out of saturation according to an adjustment routine. The adjustment routine consists of initially setting the duty cycle of the pulse waveform control signal to a minimum so as to quickly bring the amplifier out of saturation. The duty cycle is then increased in incremental steps until a maximum duty cycle is achieved. The incremental steps may be predetermined or they may be customized according to feedback from the amplifier.

In accordance with still another aspect of the invention, when the adjustment routine for the duty cycle of the pulse waveform is to be customized according to feedback from the amplifier, a low pass filter is added so as to form an envelope filter. The envelope filter temporarily removes the ECG signals so that the exponential decay of the waveform can be observed. If the output of the envelope filter is less than a threshold and is trending toward the baseline of the output, then the routine increases the duty cycle by fixed increments until either the maximum duty cycle is reached or the output of the envelope filter does not trend toward the baseline. If the output of the envelope filter is trending away from the baseline and is outside of the required dynamic range, then the duty cycle is decreased by fixed increments until the output either returns to the dynamic range or else is no longer trending away from the baseline.

In accordance with yet another aspect of the invention, a lower frequency pole of the first frequency response curve is nominally at 0.05 Hz, while the upper frequency pole of the second frequency response curve is approximately at 10 Hz. The lower frequency response curve with a pole at 0.05 Hz allows accurate monitoring of slow ECG waveforms that can occur during normal heart monitoring. The higher frequency response curve with the 10 Hz pole is fast enough to allow the amplifier of the monitoring circuit to be brought out of saturation within a predetermined amount of time. Saturation of the amplifier often occurs when a defibrillation pulse has been applied to the patient who is being monitored.

It will be appreciated that the disclosed apparatus and method for restoring the monitoring circuit of an electrocardiograph display is advantageous in that it allows the accurate full bandwidth monitoring of ECG waveforms to be restored as quickly as possible following the application of a disruptive defibrillation pulse. The digital implementation of the sliding pole for adjusting frequency response curves of the present invention also allows accurate EGG monitoring to be restored without causing erroneous QRS detect marks. Moreover, the use of the digital method provides additional circuitry advantages, such as smaller components and more accurate circuitry control.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

The present invention is directed to a method and apparatus used in a circuit for processing ECG signals so as to allow accurate monitoring of heartbeat patterns. The circuit is designed to allow ECG monitoring to be restored as quickly as possible after a disruptive defibrillation pulse has saturated the amplifiers of the circuit and electrically charged the ECG electrodes and certain body tissues. There are three main aspects of the invention which are designed to address the problems caused by the disruptive energy of a defibrillation pulse. First, the invention is able to shift the "pole" of its frequency response curve from a "slow" 0.05 Hz curve to a "fast" 10 Hz curve so that its amplifiers can quickly be brought out of saturation following a defibrillation pulse. Second, the circuit is able to accomplish this shifting of the pole by "sliding" the pole slowly from the 10 Hz curve down to the 0.05 Hz curve, so as to avoid producing erroneous QRS detect marks, as will be discussed in more detail below. Third, the circuit is able to accomplish the above features using a digitally controlled method that has distinct advantages over other implementations, as will also be discussed in more detail below.

Figure 1:
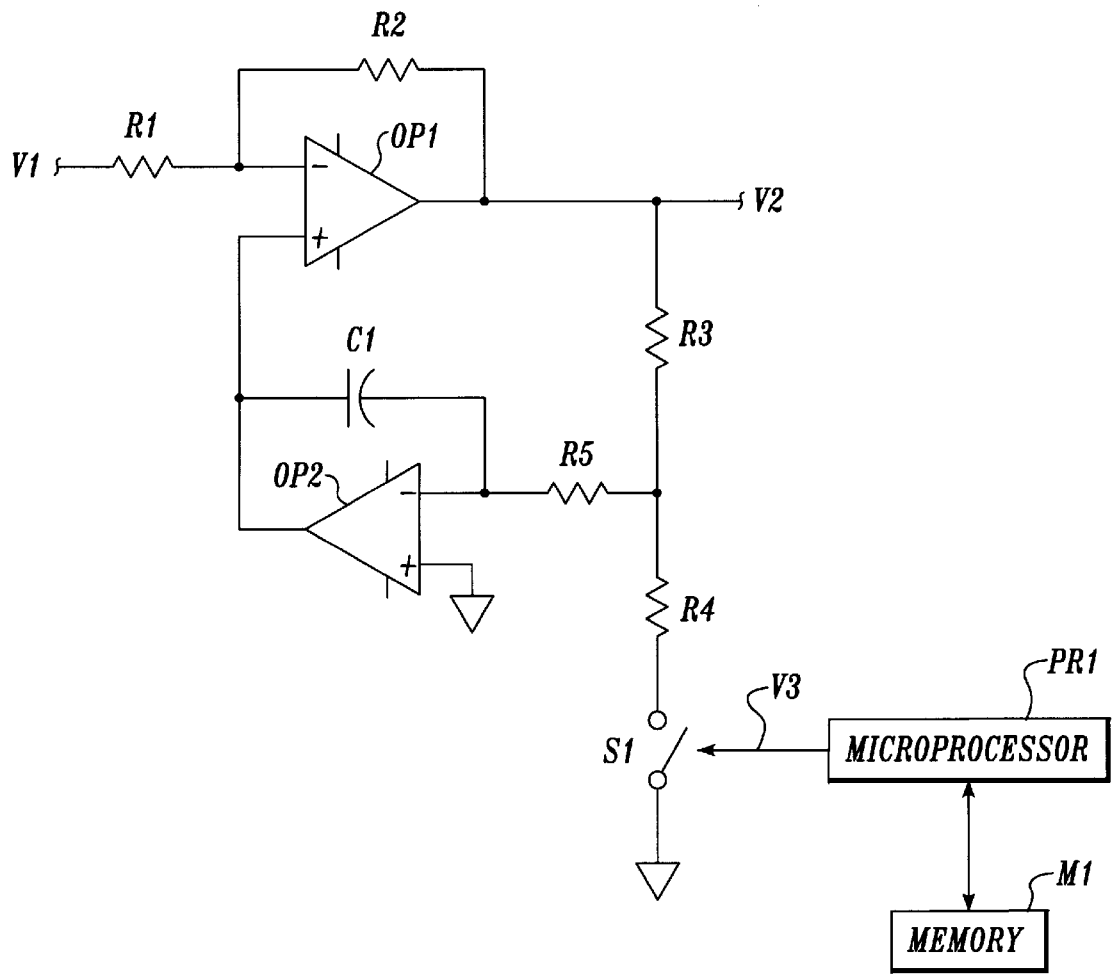
FIG. 1 is a schematic diagram of a circuit implementing the digital sliding pole fast-restore of the present invention.

A schematic representation of a circuit formed in accordance with the invention is illustrated in the attached FIG. 1. As illustrated in FIG. 1, the circuit includes resistors R1–R5, a capacitor C1, operational amplifiers OP1 and OP2, a switch S1, a microprocessor PR1, and a memory M1. An input V1 to the circuit is applied to one side of the resistor R1, and an output V2 is taken from the output of operational amplifier OP1. A control signal V3 from the microprocessor PR1 is used to control the switch S1.

The operational amplifier OP1 is used as the forward gain amplifier in the circuit. The operational amplifier OP2 is an integrator in the feedback path that is needed to provide the high pass pole of the circuit. The integrator response from operational amplifier OP2 is sufficient to filter out the clock rate of the pulse waveform that is used to control the switch S1, as described below.

The switch S1 functions essentially as a variable resistor. When the switch is open, the resistance is at infinity; and when the switch is closed, the resistance is at zero (a short circuit). When the switch is controlled with a pulse waveform signal, the amount of resistance simulated by the switch is dependent on the duty cycle of the pulse waveform. Using a digital control technique, the control signal V3 for the switch S1 is supplied by microprocessor PR1 that is controlled by software resident in memory M1. The software changes the duty cycle of the pulse waveform control signal V3 in a nonlinear manner experimentally determined to result in an ECG display that rapidly recovers, minimizes artifact presentation, and clearly shows ischemic ST segments.

Figure 2:
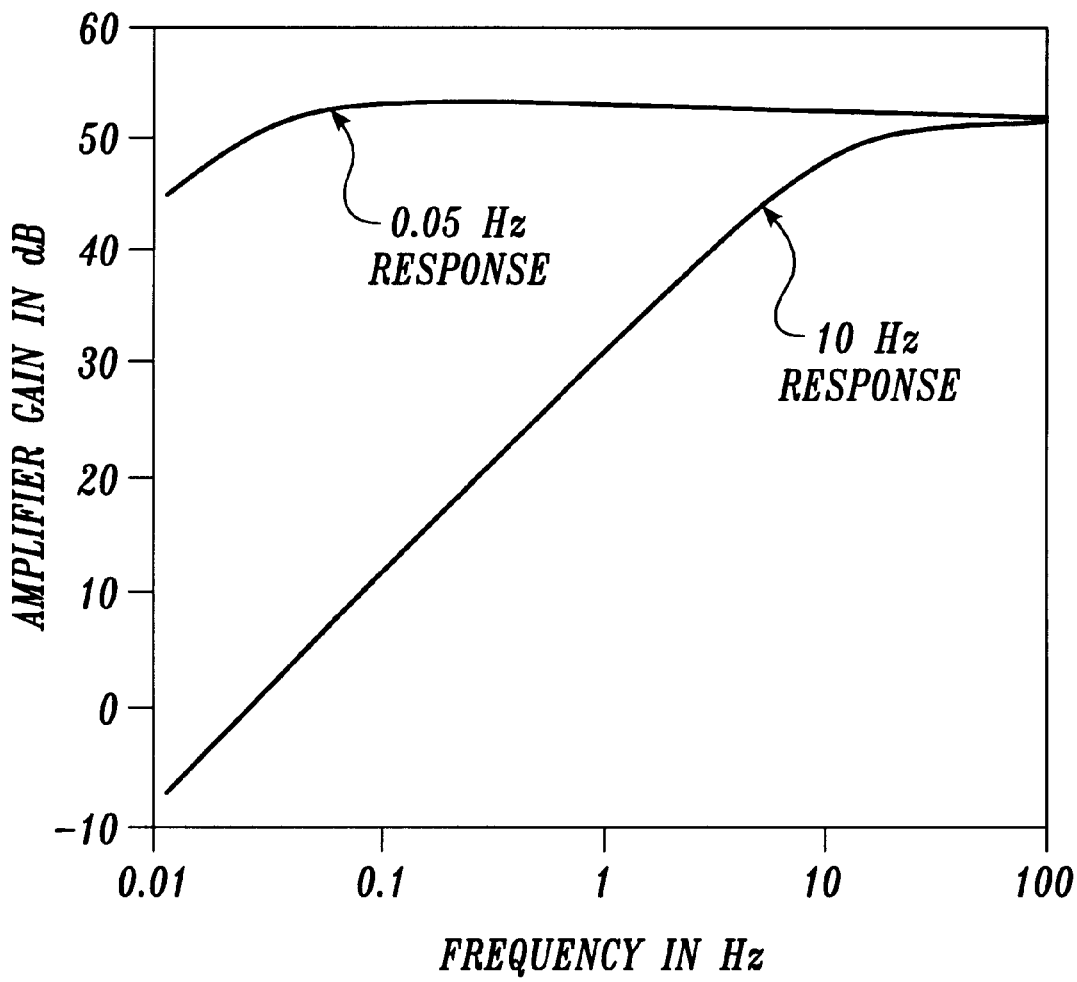
FIG. 2 shows two frequency responses curves that are implemented by a sliding pole in the circuit of FIG. 1.

FIG. 2 illustrates two possible high pass frequency response curves for the preferred embodiment circuit of FIG. 1. As is well known in signal processing, the two frequency response curves shown in FIG. 2 can be represented by "poles." The circuit is designed so that when the duty cycle of control signal V3 is adjusted to a value near zero, the high pass frequency response of the circuit is shown by the 10 Hz pole response curve. When the duty cycle of the control signal V3 is adjusted to unity, the high pass frequency response corresponds to the 0.05 Hz pole response curve. By adjusting the duty cycle of the control signal V3, the resistance simulated by the switch S1 can be varied, thus causing the pole of the high pass frequency response for the circuit of FIG. 1 to switch between the 0.05 Hz response curve and the 10 Hz response curve. As is typical in the art, ECG monitoring circuitry, such as that of the present invention, also uses a low pass filter with a corner frequency in the range of 200 Hz to 300 Hz. This low pass filter technique is well known in the art of ECG processing circuitry and will not be discussed further here.

It is desirable for a circuit such as the present invention to be able to switch its high pass pole between the 0.05 Hz and 10 Hz high pass frequency response curves. The 0.05 Hz frequency response is needed because important ECG signals exist in the 0.05 Hz range that the circuitry must be able to monitor. The 0.05 Hz frequency response is a standard for ECG processing that is promulgated by the Association for the Advancement of Medical Instrumentation (AAMI). The 10 Hz frequency response is needed when the amplifiers of the circuit are over driven to saturation (such as following a defibrillation pulse), because the 0.05 Hz response takes much too long to restore the amplifiers to normal operation. In a circuit operating with a 0.05 Hz response curve, the amplifiers could require up to 20 seconds or more to settle out (i.e., unsaturate) due to the slow response of the amplifiers. In a critical situation where abnormal heartbeat patterns are present, 20 seconds is much too long to wait for an ECG signal to reappear. However, a circuit with a 10 Hz response curve will require only about 1/10th of a second to settle out when a typical set of electrodes is being used. This is much more desirable from a signal recovery standpoint. The 10 Hz frequency response is typically used for this purpose in circuits of the prior art. Thus, by using a switching technique, the 0.05 Hz response curve can be implemented for normal ECG signal processing, and the 10 Hz response curve can briefly be implemented when a problematic high voltage saturates the amplifiers (in this case, by briefly making the control signal V3 go low). Consequently, the amplifiers of the circuit quickly return to their nonsaturated state.

Figure 3:
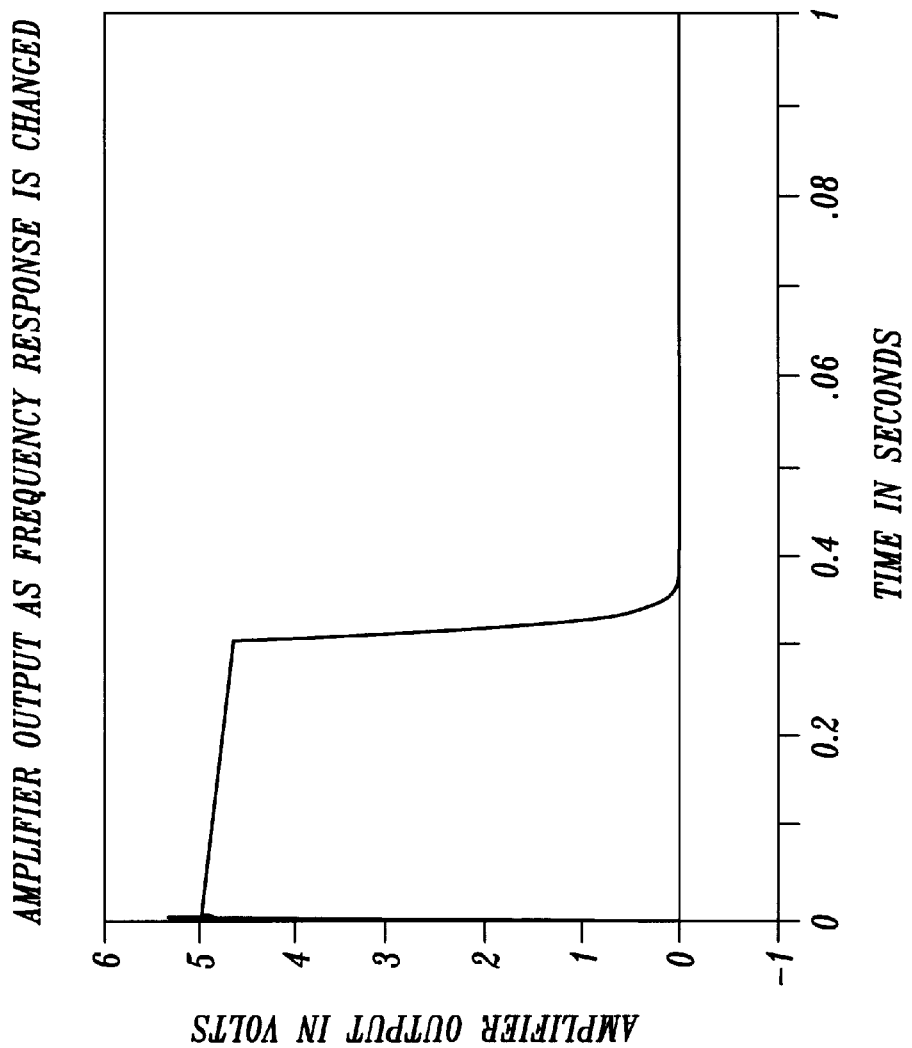
FIG. 3 shows a graph of the amplifier unsaturation process of the circuit of FIG. 1 once a saturating defibrillation pulse has been applied.

FIG. 3 illustrates the point just described. At time t=0, a high voltage input signal is introduced that nearly saturates the amplifiers of the circuit near the 5V level. Also at time t=0, the control signal V3 is high so that the frequency response curve of the circuit is at 0.05 Hz. From the time t=0 to time t=0.3, the output voltages of the amplifiers slowly decay back toward their normal state. The decay is so slow because the circuit is operating at the 0.05 Hz response curve. At this rate, the decay will take up to 20 seconds unless some change is made. At time t=0.3, the control signal V3 is made to go low so as to move the circuit to a 10 Hz response, which, as shown in FIG. 3, allows the amplifiers to rapidly return to their unsaturated state.

Figure 4:
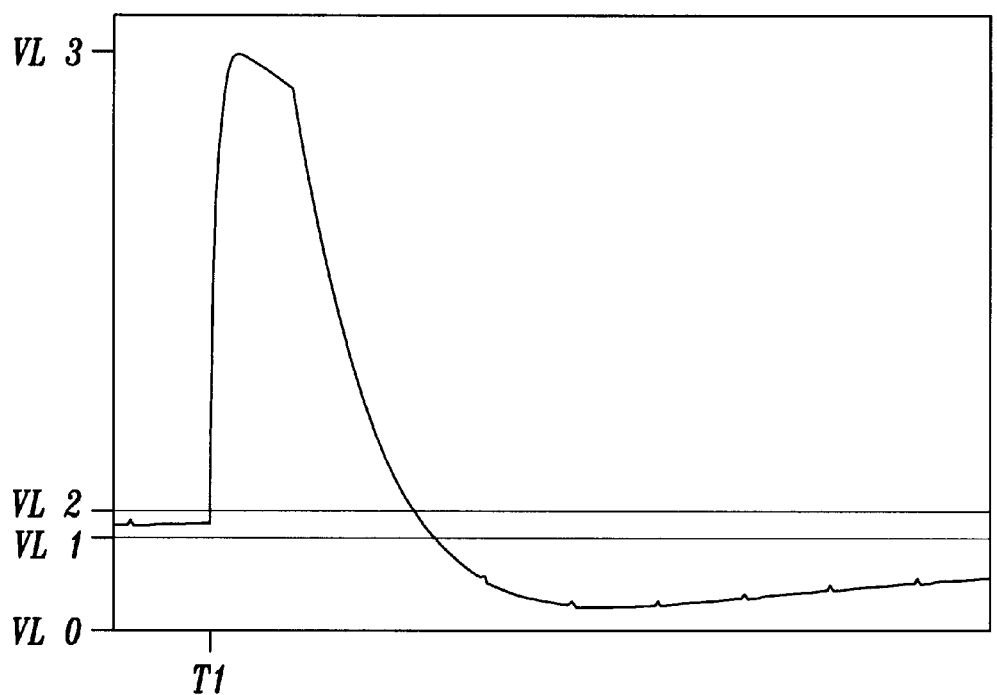
FIG. 4 shows a graph of the exponentially decaying voltage on a set of electrodes following the application of a defibrillation pulse.

FIG. 4 illustrates the type of high voltage signal that can cause the amplifiers of the circuit of FIG. 1 to be saturated. This waveform results from a typical situation where ECG electrodes have become charged due to currents drawn through them during a pace pulse or a defibrillation pulse. Once charged, the electrodes discharge over a several hundred millisecond time interval, depending upon the chemistry of the electrodes. As the electrodes discharge, the voltage across them is not DC, but rather an exponentially decaying waveform, as shown in FIG. 4. The approximately exponentially decaying waveform shown in FIG. 4 saturates the amplifiers of the ECG chart recorder and display because the amplifiers only have enough dynamic range to display signals within a voltage range between the voltage levels VL1 and VL2. As illustrated, when a defibrillation pulse occurs at time T1, the exponential waveform reaches a high voltage level VL3, and then exponentially decays to a value near voltage level VL0. The chemistry of the electrodes may affect the decaying waveform As shown, the voltage range of the exponentially decaying waveform from voltage level VL3 to VL0 is clearly in excess of the dynamic range of the amplifiers, between the voltage levels VL1 and VL2, and thus saturates the amplifiers. The electrocardiograph trace from the ECG chart recorder and display thus remains offset from the middle of the display and is unable to show full ECG waveforms until the amplifiers are again unsaturated.

The above description addresses why it is important to shift the frequency response pole of the circuit (e.g., from the slow 0.05 Hz response needed for proper ECG heart monitoring to the fast 10 Hz response needed to unsaturate the amplifiers). The problem of why this pole shift must be done relatively slowly will now be described relative to the second aspect of the invention. The second aspect of the invention, as described above, is that erroneous QRS detect marks are eliminated by incrementally sliding the frequency response pole from one position to the other.

Figure 5A:
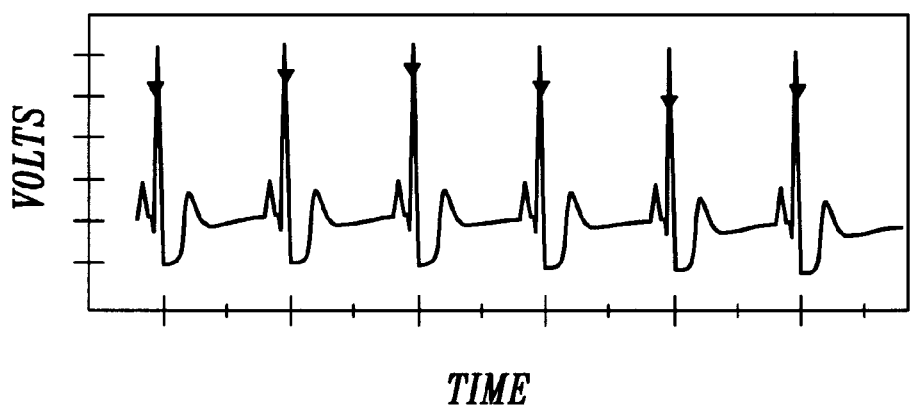
FIG. 5A shows an ischemic ECG waveform for a normal heartbeat.
Figure 5B:
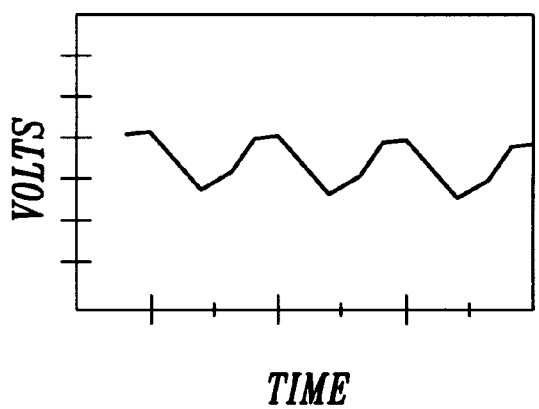
FIG. 5B shows an ECG waveform for a fibrillating heart.

FIG. 5A shows the waveform for a properly functioning, although ischemic, heart. As can be seen in FIG. 5A, triangular-shaped QRS detect marks are present at a portion of each of the high beats of the waveform signal. QRS detect marks are generated electronically by circuits that are sensitive to a particular portion of the ECG waveform which is denoted by fast rise times. It will be appreciated by those of ordinary skill in the art that such circuitry is well known and, thus, need not be disclosed herein in further detail. The presence of the QRS detect marks generally indicates a properly functioning heart. These detect marks are used by an operator to assess the health of a patient. On the other hand, FIG. 5B shows a fibrillating heart. As can be seen in FIG. 5B, no QRS detect marks are present. Thus, a key way for an operator to determine whether a heart is functioning properly or is experiencing fibrillation is by detecting QRS detect marks in the waveform.

Figure 6A:
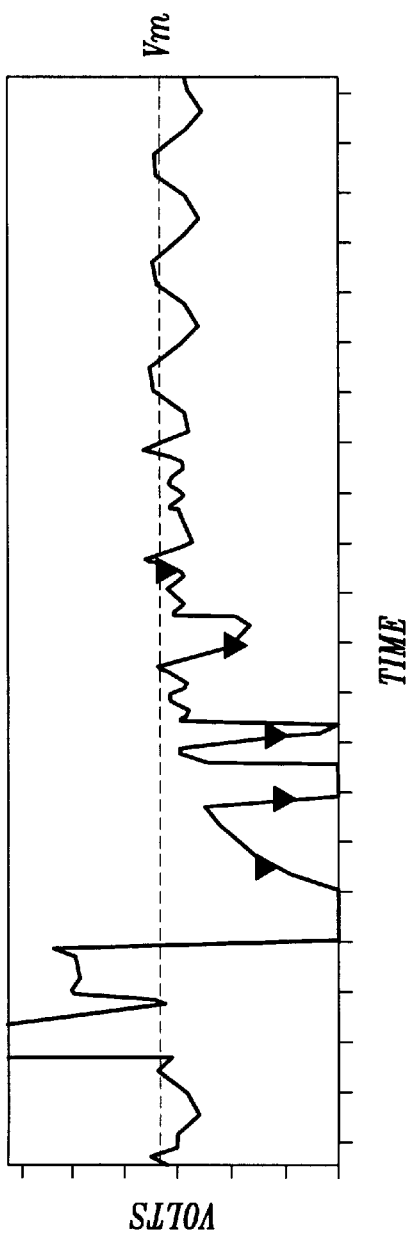
FIG. 6A shows a graph of an ECG waveform with erroneous QRS detect marks as produced by a circuit using an instantaneous switching technique.

FIG. 6A shows a waveform of a heart that, like the waveform of FIG. 5B, is experiencing fibrillation, but has also had a recent defibrillation pulse as shown in FIG. 4 applied to it. FIG. 6A shows the erroneous QRS detect marks that tend to appear in this situation if the circuit instantly switches back and forth between the 0.05 Hz response curve and the 10 Hz response curve.

Figure 6B:
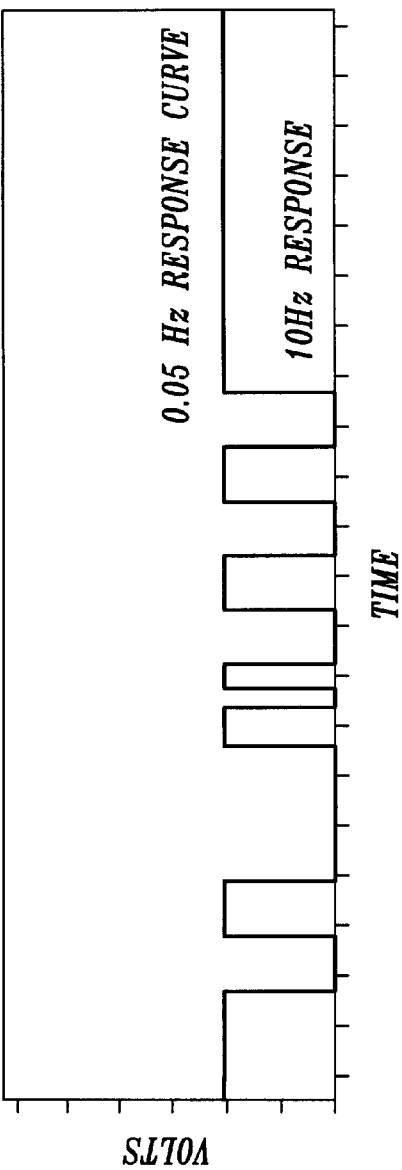
FIG. 6B shows a timing diagram for the instantaneous switching technique that produces the ECG waveform shown in FIG. 6A.

FIG. 6B illustrates a timing diagram for controlling a switch such as switch S1 in FIG. 1, using an instantaneous switching technique that produces the waveform with erroneous QRS detect marks as shown in FIG. 6A. The switching timing diagram of FIG. 6B is produced by circuitry that switches on to restore normal 0.05 Hz heart monitoring when the amplifiers are detected as operating normally, and switches off to move to the 10 Hz response when the amplifiers are detected as being saturated. The approximately exponentially decaying waveform usually has a slew rate which is in the pass band range of the 0.05 Hz high pass pole and a level large enough to drive the amplifiers into saturation. Thus, FIG. 6B switches back and forth as the amplifiers quickly unsaturate under the 10 Hz response curve, but then quickly saturate again due to the exponentially decaying waveform that is illustrated in FIG. 4. As illustrated in FIG. 6A, this phenomenon causes the output of the amplifiers to quickly rise and fall in such a way that simulates the types of waveforms that the QRS detect circuitry improperly interprets as real QRS waveforms. The QRS detect circuitry therefore produces erroneous QRS detect marks, as shown in FIG. 6A. The obvious danger of such erroneous QRS detect marks is that when an operator applies a first defibrillation pulse to a patient, the operator could interpret erroneous QRS detect marks as indicating a properly functioning heart, and consequently not apply a second defibrillation pulse.

The solution to the above-described problem that is used in one actual embodiment of the present invention is to cause the frequency response pole of the circuit to slide incrementally back from the 10 Hz response to the 0.05 Hz response over a given interval, such as over a one-second time period, rather than switching from the 10 Hz response to the 0.05 Hz response instantaneously. This "sliding pole" provides an effective compromise, in that the amplifiers are quickly restored to nonsaturation, erroneous QRS detect marks are less likely to be produced, and slow heart signals in the range of 0.05 Hz can still be effectively observed.

One means that can be used for achieving the above "sliding pole" technique is to substitute the resistor R4 and switch S1 as shown in FIG. 1 with a voltage-controlled resistor such as a transistor. By varying the voltage on the gate of the transistor, the effective resistance can be varied, thus allowing the pole to slide from the 10 Hz response to the 0.05 Hz response over a one-second interval. However, voltage-controlled resistors have poorly controlled minimum and maximum resistances, poor dynamic signal range, and poor matching of resistance versus control voltage from one device to the next. As described below, these limitations can be overcome by using a digital control technique for the switch.

Figure 7A:
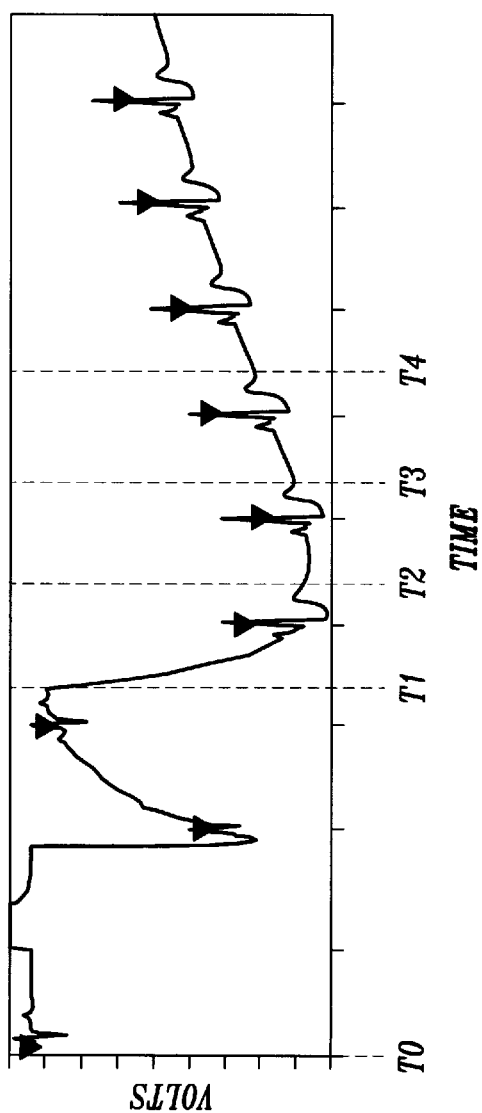
FIG. 7A shows an ECG waveform as produced by the circuit of FIG. 1 using the digital switching technique of the present invention.
Figure 7B:
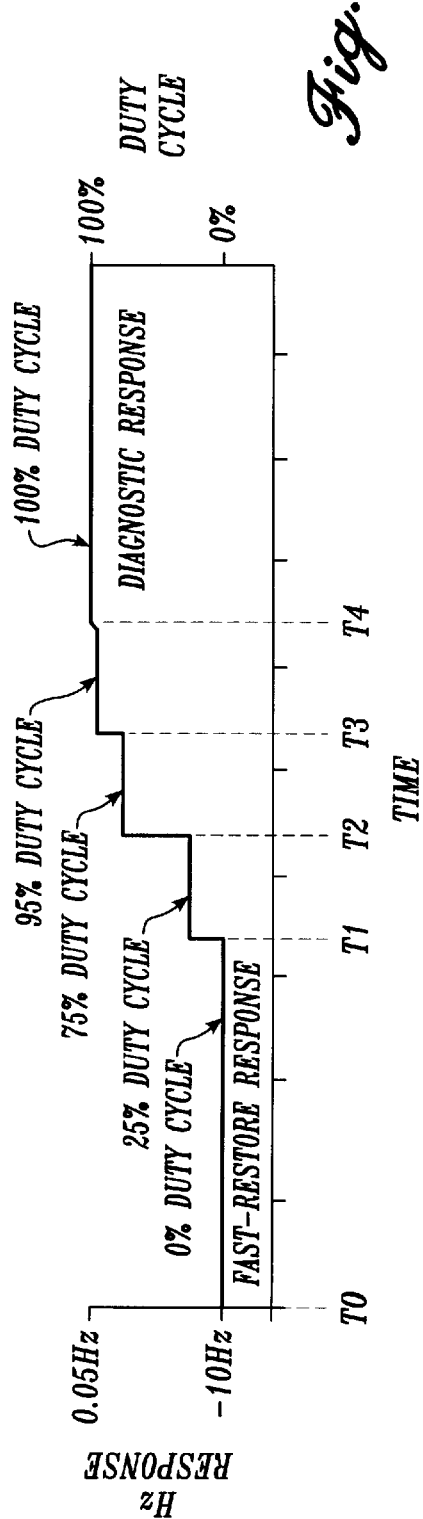
FIG. 7B shows one possible duty cycle timing diagram for the digital switching technique of the present invention that produces the waveform shown in FIG. 7A.

The alternative digitally controlled version that is used in the actual embodiment of the circuit shown in FIG. 1 includes digital software control of switch S1. The control signal V3 for the switch S1 is supplied by microprocessor PR1 which is controlled by software resident in memory M1. The duty cycle of the control signal V3 is adjusted to range from zero (when the switch S1 simulates infinite resistance) to unity (when the switch S1 simulates zero resistance). An example of this type of adjustment of the duty cycle is illustrated in FIG. 7B, as will be described in more detail below. The operating frequency of the pulse waveform is preferably above the upper frequency of the ECG bandwidth so that adjustments to the pulse waveform duty cycle do not produce erroneous QRS detect marks. In one actual embodiment, a 150 Hz limit is set in the software, following 300 Hz in the hardware. The integrator in the feedback loop of the circuit of FIG. 1 is sufficient to filter out the clock rate of the pulse waveform. The results of this implementation are very comparable to those obtained by using a voltage-controlled resistor, without the poorly controlled minimum and maximum resistances, the poorly controlled dynamic range, and the poor matching characteristics from one device to the next. In addition, the use of a digitally controlled switch S1 in this manner allows for the software to control the switch in a nonlinear manner, which is experimentally determined to produce an ECG display that rapidly recovers, minimizes artifact presentation, and clearly shows ischemic ST segments.

The foregoing result is illustrated in FIG. 7B, where at time T0 a high voltage, such as that illustrated in FIG. 4, has been introduced to the input of the amplifiers. Thus, at time T0 the circuit has switched to its 10 Hz response so as to quickly restore the amplifiers to nonsaturation. Between times T0 and T1, the control signal V3 is maintained at a 0% duty cycle. As described previously, a 0% duty cycle causes the circuit to have the 10 Hz frequency response curve. As shown at time T1, once the software or logic control has determined that the output waveform shown in FIG. 7A has reached a proper parameter (such as a given time or according to a routine such as that described below with respect to FIG. 9), the duty cycle for the pulse waveform control signal V3 is switched to a 25% duty cycle. At time T2, a 75% duty cycle is implemented, then at time T3, a 95% duty cycle is implemented, and at time T4, a 100% duty cycle is implemented. It should be noted that the method shown in FIG. 7B is in distinct contrast to the method illustrated in FIG. 6B, wherein in essence the duty cycle was instantaneously switched back and forth between a 0% duty cycle and a 100% duty cycle in such a way that produced erroneous QRS detect marks. Compared to the output waveform depicted in FIG. 7A, the output waveform produced by the method of FIG. 7B is much smoother and the QRS detect marks appear at the proper times.

In actual practice, the step values and times shown in FIG. 7B are usually more complex. The step values and times shown in FIG. 7B were chosen to approximate the recovery time of the waveform shown in FIG. 7A and are given for purposes of illustration only. The large duty cycle steps in the early part of the cycle of FIG. 7B, such as the 0 to 25% step at time T1, and the 25% to 75% step at time T2, in actual practice tend to result in significant DC stewing in the filter output waveform. While this signal remains within the required output dynamic range of the amplifiers, the large DC swings may distract a user of the ECG monitor from the real signal. Thus, in actual practice, a setting of finer resolution on the duty cycle steps may be more desirable. These finer resolution steps are easily implemented in another actual embodiment by simply adjusting the software control in the microprocessor or other logic implementation. The ease with which such adjustments can be made illustrates another advantage of the digital implementation of the present invention. As described in more detail below, FIG. 9 illustrates a preferred routine for adjusting the duty cycle steps.

Figure 8:
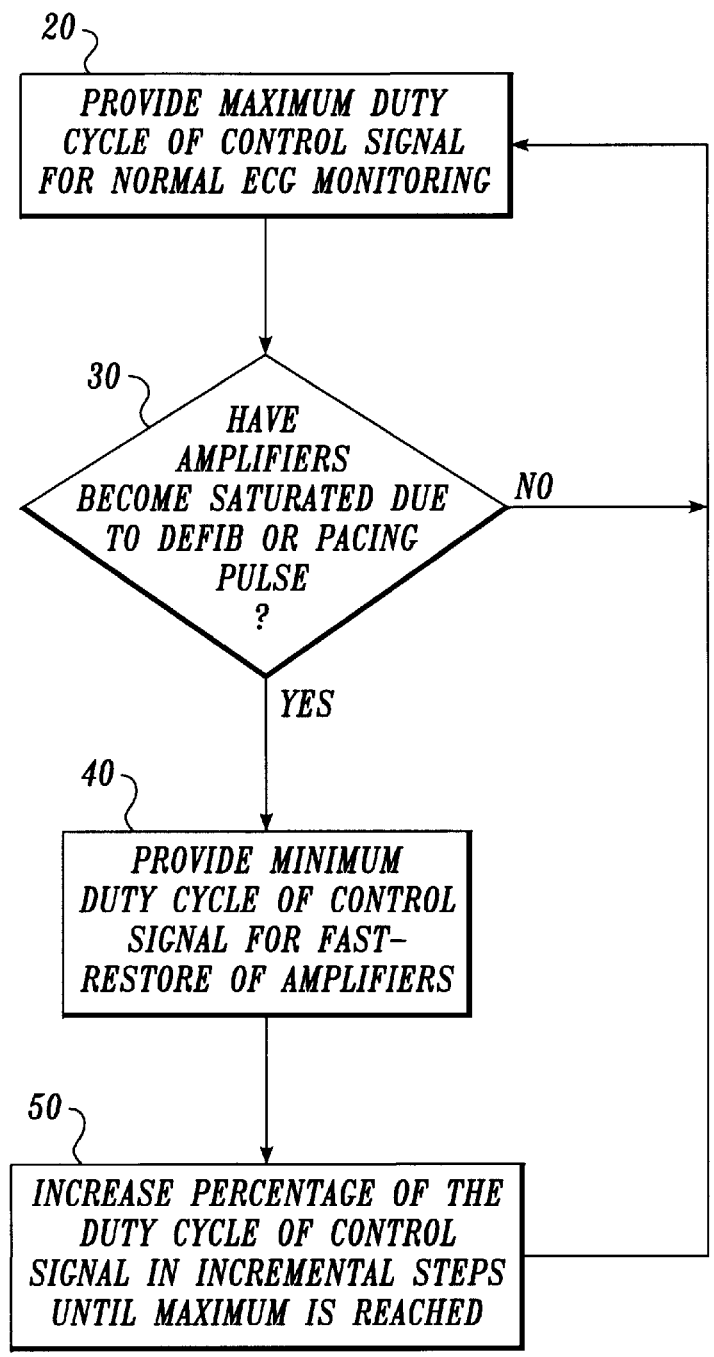
FIG. 8 is a flow chart showing the method of adjusting the duty cycle of the control signal of FIG. 1 according to the present invention.

FIG. 8 is a flow chart showing the above-described method of adjusting the duty cycle of the pulse waveform control signal so as to slide the frequency response pole according to the present invention. FIG. 8 is described under the assumption that a maximum duty cycle of the control signal causes the circuit to have the lower frequency pole for its response curve and that a minimum duty cycle causes the circuit to have the higher frequency response curve. However, it will be understood that the circuit can also be implemented so that the minimum duty cycle produces the lower frequency response curve and the maximum duty cycle produces the higher frequency response curve.

The method of FIG. 8 begins at block 20, where the circuit is operating in its normal ECG monitoring mode. Thus, at block 20, the duty cycle is at a maximum thus placing the circuit at the lower frequency response curve (e.g., the 0.05 Hz response curve in the previous example) that allows the circuit to accurately monitor the slow ECG heart signals. At a decision block 30, it is determined whether the amplifiers of the monitoring circuit have become saturated, as is often caused by defibrillation or pacing pulse being applied to the patient. If the amplifiers are not saturated, the method returns to block 20 for continued normal ECG monitoring operation. On the other hand, if the amplifiers have become saturated the method continues to a block 40. At block 40, the software or logic control of the circuit switches the duty cycle of the control signal V3 (FIG. 1) to a minimum value so as to start the fast-restore of the amplifiers to an unsaturated state. Then, at a block 50, the percentage of the duty cycle of the control signal is increased in incremental steps according to an increase routine (FIG. 9) until the maximum duty cycle is reached, at which point the method returns to block 20. The increase routine described in block 50 may be a simple method consisting of predetermined steps of percentage increases, or may be more complex, as is described below in more detail with reference to FIG. 9.

Figure 9:
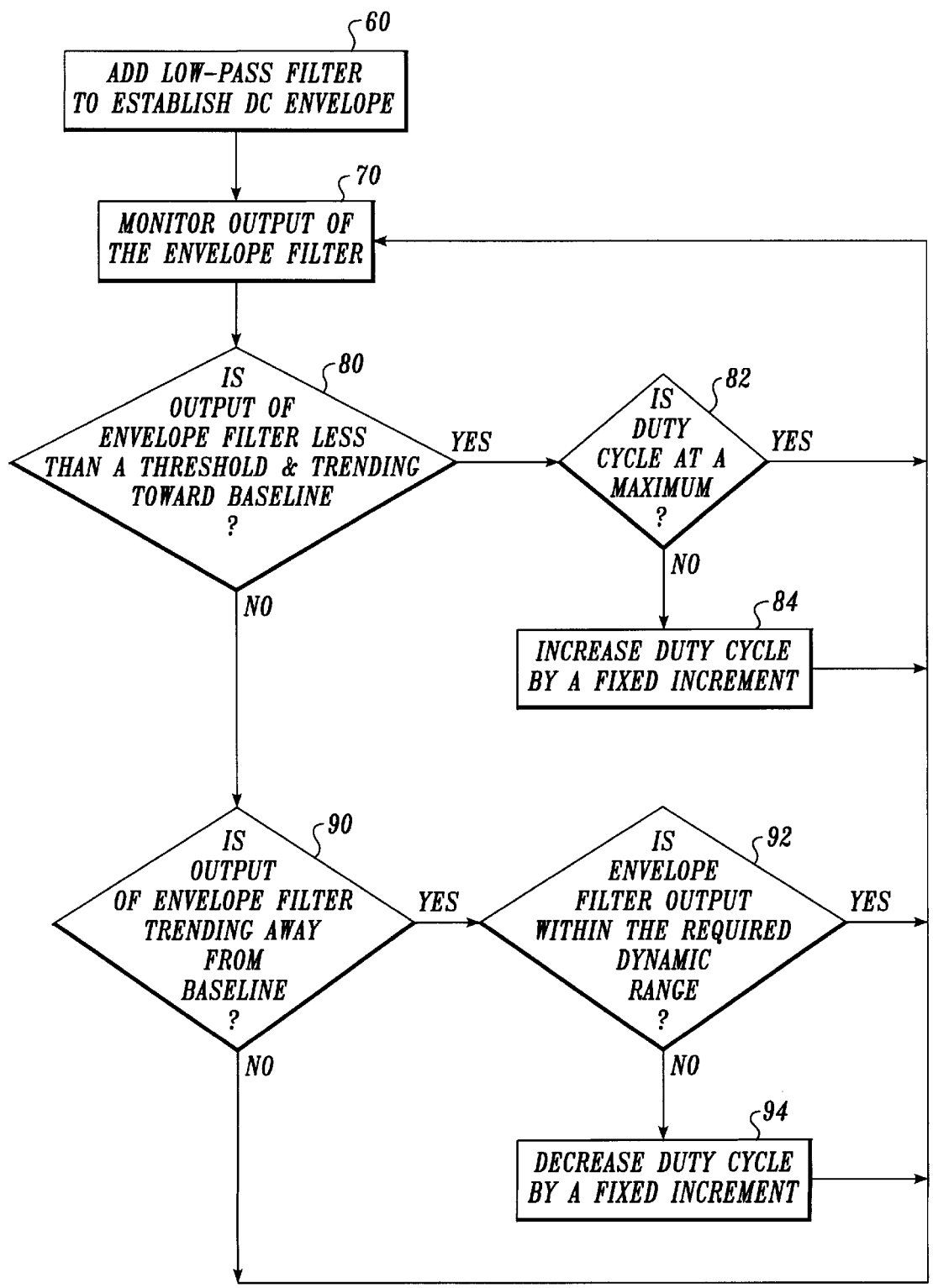
FIG. 9 is a flow chart showing an adjustment routine for adjusting the sliding pole of the present invention.

FIG. 9 illustrates an increase routine that is based on the fact that it may be desirable to use the software control of the duty cycle to adjust the sliding pole of the frequency response curve in a manner that is responsive to the particular chemistry of the electrodes that are being used. More specifically, as described above, the chemistry of the electrodes and other parameters determine the shape and size of a waveform such as that illustrated in FIG. 4. Thus, when different electrodes are used with the ECG monitoring system, there may be considerable variation in the exponential decay that needs to be overcome to restore the amplifiers to nonsaturation. Thus, a pre-chosen stepping method (such as is illustrated in FIG. 7B) may not be the most suitable for the given set of electrodes that are being used with the system. Instead, a stepping method that is responsive to certain known feedback conditions can be used to create a customized stepping routine. More specifically, one feedback condition that is generally known is that if the DC output of the high pass filter of the circuit is slewing toward the baseline, the high frequency pole is probably set too high, resulting in excessively attenuated ECG waveforms. However, if the DC output is observed as slewing away from the baseline, the high frequency pole has probably been set at too low a value. To address this problem, the sliding pole location can be adjusted on an incremental basis by the software or logic control, as described below with reference to FIG. 9, so that the circuit can best restore the amplifiers to nonsaturation without DC slewing.

As shown in FIG. 9, at a block 60 a low pass filter, as is well known in the art, is switched into the circuit so as to establish a DC envelope. Then, at a block 70 the output of the envelope filter is monitored. At a block 80, the routine determines if the envelope filter output is less than a threshold value and is trending toward the baseline. If the answer from block 80 is yes, then the routine continues to a decision block 82, where it is determined if the duty cycle of the control signal V3 is already at a maximum. If signal V3 is already at a maximum, the routine returns to block 70. If the result of decision block 82 is negative, the routine continues to a block 84. At block 84, the duty cycle is increased by a fixed increment, and then the routine returns to block 70. In this manner, continuous monitoring and increasing of the duty cycle by fixed increments is repeated through the loop between blocks 70 to 84 until either a maximum duty cycle is reached or else the envelope filter output begins to trend away from the baseline. If the envelope filter output is within required dynamic range, then the routine returns to block 70 where the duty cycle should be kept at a fixed value and it is expected that recovery should occur shortly with no adjustment.

Returning to block 80, if the output of the envelope filter is not determined to be less than a threshold and is not trending toward the baseline, the routine continues to a block 90. At block 90, it is determined if the output of the envelope filter is trending away from the baseline. If the output is not trending away, the routine returns to block 70. However, if the output is trending away, the routine continues to a block 92. At block 92 it is determined if the envelope filter output is within a required dynamic range. If the envelope filter output is outside of the required dynamic range, then the method continues a block 94 where the duty cycle is decreased by a fixed increment, after which the routine returns to block 70. In this manner, the envelope filter output continues to be monitored, and the duty cycle continues to be decreased by fixed increments through the loop between blocks 70 and 94 until the envelope filter output is no longer trending away from the baseline. The logic implemented in block 94 will rarely be used because it is expected that once the output of the envelope filter is trending away from the baseline, it will be within the required dynamic range, thus returning from block 92 to block 70.

The above-described invention is a circuit that provides an ECG output in an accurate and efficient manner. Through the use of the digital sliding pole, the circuit recovers to a near zero baseline error in a minimal amount of time, while still providing accurate ECG waveforms. The pole location is controlled by the duty cycle of the switch control signal. This implementation has results that are very comparable to those of using a voltage controlled resistor, without the poorly controlled minimum and maximum resistances, the poorly controlled dynamic range, and the poor matching of resistance versus control voltage from one device to the next. In addition, the use of a digitally controlled switch in this manner allows for software control that can be upgraded and adjusted as described above. This software control further allows the resolution of the duty cycle steps to be adjusted in any increments and can be done so as to avoid slewing of the DC output.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A circuit for processing ECG signals, the circuit comprising:

an amplifier for amplifying the ECG signals;

a switch coupled to the amplifier, the switch being switchable between at least two positions, the position of the switch determining the high pass frequency response of the circuit, the switch being controlled by a switch control signal;

the switch in a first position causing the circuit to have a first high pass frequency response curve with a first pole that is low enough to allow processing of ECG signals;

the switch in a second position causing the circuit to have a second high pass frequency response curve with a second pole that is high enough to cause the amplifier of the circuit to be brought out of saturation within a specified period of time;

a control program for providing the switch control signal, the switch control signal being a pulse waveform with a duty cycle, the duty cycle being adjusted in incremental steps by the control program so as to shift the high pass frequency response of the circuit in incremental steps from the second frequency response curve to the first frequency response curve; and the control program including an adjustment routine that switches the switch to the second position and then adjusts the duty cycle of the switch control signal in incremental steps until the first frequency response curve is exhibited.

2. The circuit of claim 1, further comprising a low pass filter coupled to the amplifier, the low pass filter being added to establish a DC envelope filter with an output, and also comprising a monitoring means coupled to the low pass filter for monitoring the output of the envelope filter and providing related data.

3. The circuit of claim 2, wherein the output from the envelope filter has a baseline and the adjustment routine uses data from the monitoring means to determine if the output of the envelope filter is trending toward the baseline and, if it is, controlling the switch to change the duty cycle by fixed increments to reduce the frequency of the pole of the high pass frequency response curve so as to shift the pole in a direction going away from the second pole until either the output of the envelope filter is no longer trending toward the baseline or a predetermined limit for the duty cycle of the control signal is reached.

4. The circuit of claim 2, wherein the output from the envelope filter has a baseline and a required dynamic range and the adjustment routine uses data from the monitoring means to determine if the output of the envelope filter is trending away from the baseline and is outside of the required dynamic range and, if it is, the switch control signal controlling the switch to change the duty cycle of the control signal by fixed increments to increase the frequency of the pole of the high pass frequency response curve in a direction going toward the second pole until either the output of the envelope filter is no longer trending away from the baseline or the output of the envelope filter comes within the required dynamic range or a limit for the duty cycle of the control signal is reached.

5. The circuit of claim 1, wherein the incremental steps comprise at least three steps of progressive duty cycle percentages between unity and zero duty cycle values, comprising at least a step to a 25% duty cycle, a step to a 75% duty cycle, and a step to a 95% duty cycle.

6. The circuit of claim 1, wherein the circuit further comprises an output with DC slewing and the incremental steps comprise a sufficient number of steps of duty cycle changes so that the DC slewing of the output of the circuit that is caused by the steps does not exceed a selected level.

7. The circuit of claim 1, wherein the first pole of the first frequency response curve is at approximately 0.05 Hertz.

8. The circuit of claim 1, wherein the second pole of the second frequency response curve is at approximately 10 Hertz.

9. A circuit for processing ECG signals, the circuit comprising:

an amplifier for amplifying the ECG signals;

a switch coupled to the amplifier, the switch being switchable between at least two positions, the position of the switch determining the high pass frequency response curve of the circuit, the switch being controlled by a switch control signal;

the switch in a first position causing the circuit to have a first high pass frequency response curve with a first pole that is low enough to allow processing of ECG signals;

the switch in a second position causing the circuit to have a second high pass frequency response curve with a second pole that is high enough to cause the amplifier of the circuit to be brought out of saturation within a specified period of time;

a control program for providing the switch control signal, the switch control signal being a pulse waveform with an operating frequency and a duty cycle, the duty cycle being adjusted in incremental steps by the control program so as to shift the high pass frequency response of the circuit in incremental steps from the second frequency response curve to the first frequency response curve; and a QRS detect mark generator coupled to the amplifier, wherein the operating frequency of the pulse waveform is above the upper frequency of a typical ECG bandwidth as a result of which adjustments to the pulse waveform duty cycle do not cause the QRS detect mark generator to produce erroneous QRS detect marks.

10. A high pass filter for processing ECG signals, the high pass filter comprising:

an output for providing the processed ECG signals;

an amplifier coupled to the output;

a control means for providing a pulse waveform with an adjustable duty cycle having at least a first level and a second level, the duty cycle of the pulse waveform determining the pole of the high pass frequency response curve of the high pass filter, the duty cycle at the first level adjusting the pole of the high pass filter to a frequency of approximately 0.05 Hertz, the duty cycle at the second level adjusting the pole of the high pass filter to a frequency that is greater than 0.05 Hertz; and the control means including an adjustment routine that sets the duty cycle at the second level and then adjusts the duty cycle in incremental steps so as to shift the duty cycle from the second level to the first level.

11. The high pass filter of claim 10, wherein when the duty cycle is at the second level, the pole of the high pass filter is at approximately 10 Hertz.

12. The high pass filter of claim 10, further comprising a QRS detect mark generator coupled to the output, and wherein the pulse waveform comprises an operating frequency that is above the upper frequency of a typical ECG bandwidth as a result of which adjustments to the duty cycle of the pulse waveform by the control means do not cause the QRS detect mark generator to produce erroneous QRS detect marks.

13. A circuit for processing ECG signals, ECG signals having a typical bandwidth with an upper frequency, the circuit comprising:

a control circuit for providing a pulse waveform control signal with a duty cycle;

a high pass filter with an adjustable pole coupled to the control circuit;

an output coupled to the high pass filter for outputting processed ECG signals; and a QRS detect mark generator coupled to the output, the pole of the high pass filter being adjustable by the pulse waveform control signal that is provided by the control circuit, the pulse waveform having an operating frequency that is above the upper frequency of a typical ECG bandwidth as a result of which adjustments to the duty cycle of the pulse waveform by the control circuit do not cause the QRS detect mark generator to produce erroneous QRS detect marks at the output of the circuit.

14. The circuit of claim 13, wherein the control circuit comprises a control adjustment circuit for adjusting the duty cycle and the control circuit further comprises an ECG signal processing period and a circuit recovery period, the control circuit cycling through the ECG signal processing period and the circuit recovery period and wherein during the ECG signal processing period the duty cycle of the control signal is adjusted by the control adjustment circuit to a first level so that the pole of the high pass filter is set at a frequency of approximately 0.05 Hertz so as to allow normal ECG signal processing.

15. The circuit of claim 14, wherein the high pass filter comprises an amplifier, and wherein during the circuit recovery period the duty cycle of the control signal is adjusted by the control adjustment circuit to a second level so that the pole of the high pass filter is at a frequency of approximately 10 Hertz, so as to allow the amplifier in the high pass filter to quickly be brought out of saturation.

16. A method for bringing an amplifier out of saturation in an ECG monitoring circuit, the ECG monitoring circuit having at least a first frequency response curve with a first pole for normal ECG signal processing and a second frequency response curve with a second pole for fast circuitry recovery, the circuit being controlled to move between the two frequency response curves by a pulse waveform control signal with a duty cycle that is generated by a control circuit, the circuit having the first frequency response curve when the duty cycle of the control signal is at a first level and the circuit having the second frequency response curve when the duty cycle of the control signal is at a second level, the method comprising:

(a) detecting when the amplifier has become saturated and then initially providing the pulse waveform control signal with the duty cycle of the second level; and (b) using an adjustment routine to change the percentage of the duty cycle of the pulse waveform control signal in incremental steps from the second level to the first level, thus returning the circuit to normal ECG signal processing when the duty cycle is returned to the first level.

17. The method of claim 16, wherein the ECG monitoring circuit has DC slewing caused by the incremental steps, and wherein the number of incremental steps used by the adjustment routine is increased until the DC slewing of the ECG monitoring circuit that is caused by the steps is reduced to a selected level.

18. The method of claim 16, wherein the pulse waveform has an operating frequency that is set at a frequency that is above the upper frequency of a typical ECG bandwidth.

19. The method of claim 16, wherein the adjustment routine comprises:

(a) adding a low pass filter to establish a DC envelope filter with an output that has a baseline and a required dynamic range;

(b) monitoring the output of the envelope filter;

(c) if the output of the envelope filter is less than a threshold and trending toward the baseline, verifying whether the duty cycle of the control signal is already at a maximum and, if it is, returning to (b) and, if it is not, proceeding to (d); and (d) increasing the duty cycle by a fixed increment and then returning to (b).

20. The method of claim 19, further comprising the steps of determining if the output of the envelope filter is trending away from the baseline and if it is outside the required dynamic range and, if it is, decreasing the duty cycle by a fixed increment and then returning to step (b) of claim 19.

21. In an ECG monitoring circuit with a high pass frequency response curve with a pole, a method for adjusting the pole of the high pass frequency response curve, the ECG monitoring circuit including an amplifier and a means for determining when the amplifier is saturated, the pole of the high pass frequency response curve being adjustable by a control circuit that produces an adjustable pulse waveform control signal with a duty cycle, the pole being at a first frequency for normal ECG monitoring when the duty cycle is at a first level and being at a second frequency for fast unsaturation of the amplifier when the duty cycle is at a second level, the method comprising:

(a) placing the duty cycle at the first level for normal ECG signal monitoring;

(b) determining when the amplifier is saturated;

(c) when the amplifier is saturated, changing the duty cycle to the second level for fast unsaturation of the amplifier; and (d) returning the duty cycle from the second level to the first level in incremental steps.

22. The method of claim 21, wherein normal ECG signals have an upper bandwidth and wherein the pulse waveform control signal has a frequency that exceeds the frequency of the upper bandwidth of normal ECG signals.

23. The method of claim 21, wherein an adjustment routine is used to create an envelope filter with an output, and wherein the adjustment routine uses the output of the envelope filter to determine the number of incremental steps that are used to return the duty cycle from the second level to the first level.

* * * * *

UNITED STATES PATENT AND TRADEMARK OFFICE
CERTIFICATE OF CORRECTION

PATENT NO. : 6,185,450 B1
DATED : February 6, 2001
INVENTOR(S) : D.R. Seguine et al.

It is certified that error appears in the above-identified patent and that said Letters Patent is hereby corrected as shown below:

<u>Title page, item [56],</u>
References Cited (U.S Patents), insert in appropriate numerical order the following:
-- 4,494,551   1/1985      Little, III et al.
   5,357,969   10/1994     Herleikson --
References Cited (U.S Patents), insert in appropriate numerical order the following:
-- 4,147,990   4/1979      Dokus et al.--

References Cited (Foreign Patents) insert in appropriate numerical order the following:
  -- FOREIGN PATENT DOCUMENTS
0486399A    EP    5/1992
2153084A    GB    8/1985 --

References Cited (Other Publications) insert in appropriate numerical order the following:
-- International Search Report, PCT/US99/01611, May 26, 1999. --

<u>Column 10,</u>
Line 59, "reponse of" should read -- response curve of --

Signed and Sealed this

Eleventh Day of September, 2001

Attest:

NICHOLAS P. GODICI
*Acting Director of the United States Patent and Trademark Office*

*Attesting Officer*